United States Patent [19]

Adams, Jr.

[11] Patent Number: 4,620,527
[45] Date of Patent: Nov. 4, 1986

[54] ENDOSCOPE CONTAINER AND SUPPORT APPARATUS

[76] Inventor: Paul R. Adams, Jr., 600 W. Avalon St., Apt. 275, Longview, Tex. 75603

[21] Appl. No.: 688,878

[22] Filed: Jan. 4, 1985

[51] Int. Cl.⁴ .................... A61L 2/26; B08B 11/02
[52] U.S. Cl. ......................... 128/4; 206/305; 206/822; 248/151
[58] Field of Search ............ 128/4, 6; 206/305, 524.5, 206/570, 571, 572, 822, 828; 220/85 H; 248/151, 161, 176, 177

[56] References Cited

U.S. PATENT DOCUMENTS

| | | | |
|---|---|---|---|
| 577,829 | 2/1897 | Brown | 248/151 X |
| 900,180 | 10/1908 | Maggini | 248/151 X |
| 2,767,513 | 10/1956 | Bluestone | 248/151 X |
| 3,963,438 | 6/1976 | Banez | 128/6 X |
| 4,474,174 | 10/1984 | Petruzzi | 128/4 |

Primary Examiner—William H. Grieb
Attorney, Agent, or Firm—John M. Harrison

[57] ABSTRACT

An endoscope container and support apparatus for supporting the control head and containing the flexible shaft of a fiber optic flexible endoscope, which apparatus is characterized by a container having an open top and a curved bottom designed to receive and contain the flexible shaft of the endoscope, with a stopper or plug closing the open top, a hollow yoke rest inserted through the stopper, with the upper end of the yoke rest shaped for supporting the control head of the endoscope, and a ring support fitted with telescoping legs for encircling and supporting the container.

14 Claims, 4 Drawing Figures

U.S. Patent  Nov. 4, 1986  4,620,527
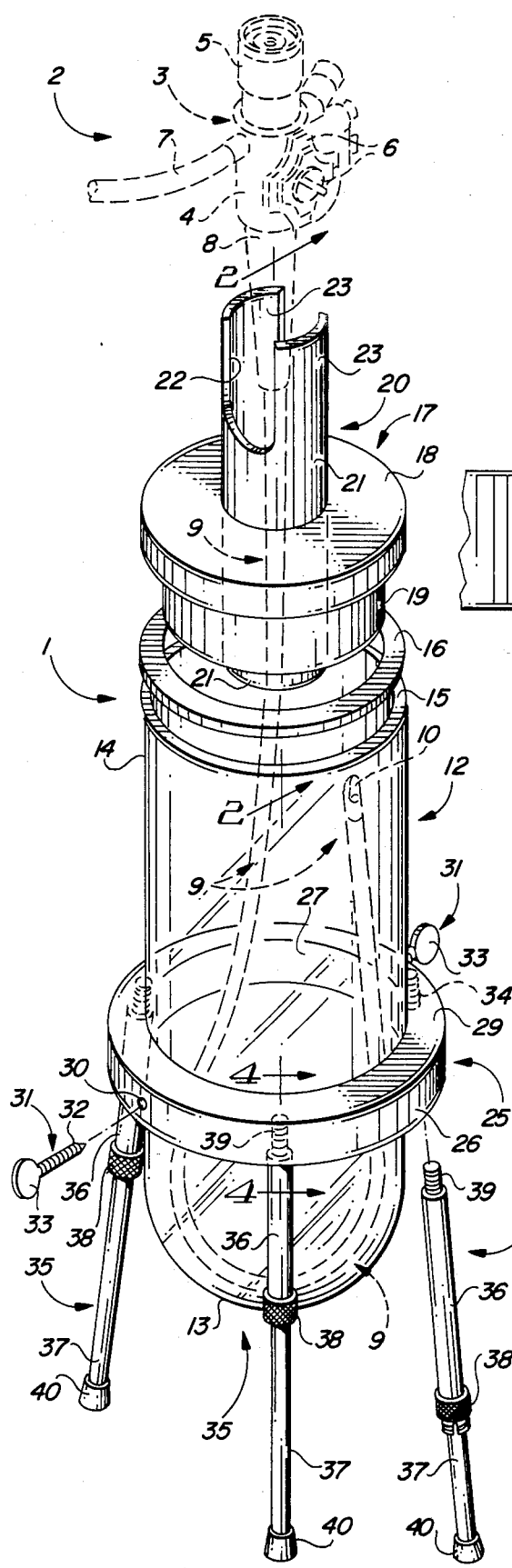
FIG.1
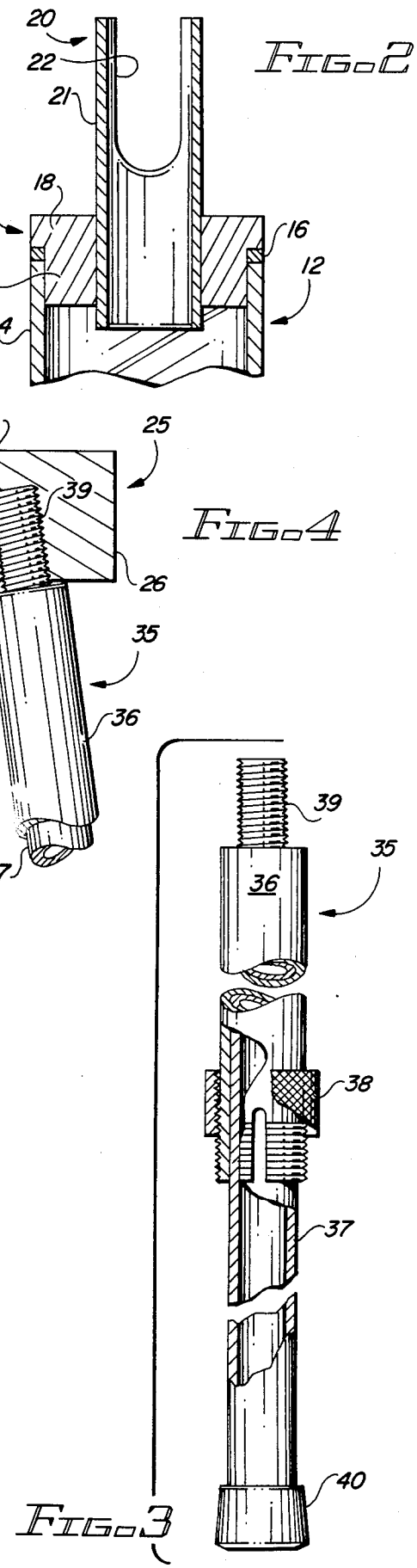
FIG.2
FIG.4
FIG.3

ENDOSCOPE CONTAINER AND SUPPORT APPARATUS

BACKGROUND OF THE INVENTION

1. Field of the Invention

This invention relates to fiber optic endoscope devices and more particularly, to a container and support apparatus for supporting the control head of a fiber optic endoscope and containing the flexible shaft of the endoscope. The container and support apparatus of this invention is characterized in a preferred embodiment by a generally tubular-shaped container having an open top and a curved bottom, a stopper or plug inserted in the open top of the container and sealed by means of an O-ring, a hollow yoke rest inserted through the stopper for guiding the flexible shaft into the container, with the top end of the yoke rest shaped to receive the control head of the endoscope and a shaped ring adjustably supporting the container and provided with telescoping legs for further adjusting the height of the container and the supported endoscope. In one embodiment of the invention a disinfectant such as providone iodine, commonly called betadine, can be added to the container and the flexible shaft of the endoscope, which is coiled or looped in the container, is immersed in the disinfectant solution, in order to provide a means for both storing and disinfecting the flexible shaft of the endoscope.

Flexible endoscope devices which incorporate fiber optics for viewing deep body cavities are rapidly becoming well known and are now commonly used in medical diagnostic procedures. Such endoscopes are characterized by a tubular fiber optic light transmitting means and viewing mechanism, whereby the body cavity under investigation can be inspected. The viewing mechanism is normally located in a control head which is fitted with appropriate directional and lighting controls to manipulate the distal end or tip of a flexible shaft in a desired configuration within the body cavity. Some endoscopes are also fitted with means for accommodating surgical instruments and liquid fittings for flushing the body cavity with water.

2. Description of the Prior Art

One of the problems associated with fiber optic endoscopes is the difficulty of efficiently supporting and storing the devices, as well as disinfecting and locating the long, flexible shaft of the endoscope. The flexible shaft must be disinfected after each use and storage sometimes presents a problem due to the length and the flexibility of the shaft. The disposition and storage of fiber optic endoscopes such as the endoscope disclosed in U.S. Pat. No. 4,474,174, dated Oct. 2, 1984, to Claude E. Petruzzi, when the endoscope is not in use has taken several forms. A shaped supporting shelf is disclosed in the Sandspur Enterprises, Inc. catalogue, which rack includes a primary indentation for supporting the control head of the endoscope and other indentations for supporting other elements of the endoscope. An alternative means for both supporting and disinfecting endoscopes is disclosed in the Olympus catalogue, which details a portable trolley described as a "complete accessory and auxiliary back-up for endoscopic procedures". The trolley includes a shaped groove located on a top surface, which groove is designed to receive the control head and the flexible shaft of the endoscope. A "KC-10 Mobile Disinfecting Station" is also disclosed and is also provided with a groove for containing disinfectant and shaped to both contain and disinfect the flexible shaft of the endoscope when the endoscope is not in use.

One of the problems associated with the prior art techniques for supporting endoscope devices is the relatively large space necessary for containing the flexible shaft; for example, in the case of the rack noted in the Sandspur Enterprises catalogue, the flexible shaft must extend below the rack and occupies considerable wall space. A problem associated with the Olympus disinfecting station is that of spilling the disinfecting fluid provided in the shaped groove in the top surface of the tray while the station is being relocated. Accordingly, it is an object of this invention to provide a new and improved endoscope container and support apparatus which is small and is characterized by a shaped container having an open end and a round bottom for receiving and bending, coiling or looping the flexible shaft of an endoscope, a stopper or plug fitted in the open end of the container, with a shaped yoke rest inserted through the stopper and communicating with the interior of the container for inserting the flexible shaft into the container and supporting the control head of the endoscope and a supporting ring provided with legs for supporting the container.

Another object of this invention is to provide a new and improved endoscope container and support apparatus which includes a transparent container having a round bottom and an open top for receiving and automatically bending, coiling or looping the flexible shaft of an endoscope, the container adjustably resting on a ring support provided with supporting legs, with a shaped yoke extending through a stopper provided in the open end of the container for guiding the flexible shaft into the container and supporting the control head of the endoscope.

Another object of this invention is to provide an endoscope container and support apparatus which is characterized by a transparent, tubular-shaped member having a curved bottom and an open top for receiving and containing the flexible shaft of an endoscope, a stopper closing the open end of the container and provided with a yoke rest communicating with the container interior for guiding the flexible shaft into the container and receiving and supporting the control head of the endoscope and a support ring provided with telescoping legs and thumb screws, for receiving and supporting the container and the endoscope at a selected height with respect to a supporting surface.

Still another object of this invention is to provide a supporting device for fiber optic endoscopes which includes a tubular, transparent glass or plastic container having a curved bottom and an open top for receiving, bending and optionally disinfecting and storing the flexible shaft of an endoscope, a stopper sealed by an O-ring closing the open top of the container, the stopper further provided with a shaped yoke for guiding the flexible shaft into the container and receiving and supporting the control head of the endoscope when the flexible shaft of the endoscope is extended in a U-shaped configuration inside the container, and further including a ring support encircling the container and provided with telescoping legs and thumb screws for supporting the container and the endoscope at a selected height with respect to a supporting surface.

SUMMARY OF THE INVENTION

These and other objects of the invention are provided in an endoscope container and support apparatus for supporting the control head and storing and disinfecting the flexible shaft of a fiber optic endoscope device, which apparatus includes, in a preferred embodiment, a transparent, generally tubular-shaped container having a curved bottom and an open top for receiving and bending or coiling the flexible shaft, with a stopper closing and sealing the top of the container, and a hollow, shaped yoke rest extending through the stopper and having one end communicating with the interior of the container for guiding the flexible shaft into the container and supporting the control head of the endoscope, and further including a ring encircling and supporting the container and provided with thumb screws and angular-mounted, telescoping legs for supporting the container and the endoscope at a selected height above a supporting surface.

BRIEF DESCRIPTION OF THE DRAWING

The invention will be better understood by reference to the accompanying drawing, wherein:

FIG. 1 is a perspective view of a preferred embodiment of the endoscope container and support apparatus of this invention;

FIG. 2 is a sectional view, taken along line 2—2 in FIG. 1, of a preferred yoke rest and stopper used in the endoscope container and support apparatus;

FIG. 3 is a sectional view, taken along line 3—3 in FIG. 1, of a preferred telescoping leg; and FIG. 4 is a side view, partially in section, of a preferred telescoping leg threaded into the ring support.

DESCRIPTION OF THE PREFERRED EMBODIMENTS

Referring to FIGS. 1 and 2 of the drawing in a preferred embodiment of the invention, the endoscope container and support apparatus is generally illustrated by reference numeral 1 and is designed to support a flexible endoscope 2, illustrated in phantom and provided with a control head 3 and a flexible shaft 9 extending from the control head 3. The control head 3 of the flexible endoscope 2 is further characterized by a body 4 and eyepiece 5, control wheels 6 and a universal cord 7, which is attached to other control apparatus (not illustrated) used in connection with the flexible endoscope 2. A tube base 8 extends from the body 4 and connects the body 4 to the flexible shaft 9, as illustrated in FIG. 1. A distal end 10 is provided on the extending end of the looped flexible shaft 9. The endoscope container and support apparatus 1 is further characterized by a generally tubular-shaped, transparent container 12, having a curved bottom 13 and an upward standing wall 14, which terminates in a lip 15. An O-ring 16 is positioned adjacent the lip 15 and a stopper 17, shaped to define a stopper flange 18 and a stopper base 19, is designed to close the open end of the container 12 at the lip 15. Accordingly, when the stopper base 19 of the stopper 17 is inserted inside the container 12, with the stopper flange 18 seated against the O-ring 16 and the O-ring 16 is tightly pressed against the lip 15 of the container 12, the stopper 17 closes and seals the container 12 at the lip 15. Alternatively, the O-ring 16 can be omitted, under circumstances where the stopper 17 is manufactured of a resilient, self-sealing material such as rubber or plastic, according to the knowledge of those skilled in the art. A hollow yoke rest 20 extends through the stopper flange 18 and the stopper base 19 of the stopper 17 and communicates with the interior of the container 12, as illustrated in FIG. 2. The yoke rest 20 is provided with a generally tubular-shaped yoke body 21, having a pair of upward standing, oppositely-disposed support fingers 23, defined by a saddle-shaped slot 22. The slot 22 in the yoke rest 20 is configured to receive the body 4 and the universal cord 7 of the control head 3, in order to support the control head 3 of the flexible endoscope 2. The tube base 8 of the flexible endoscope 2 extends inside the hollow interior of the yoke rest 20 and the flexible shaft 9 is looped inside the container 12 by contact with the curved bottom 13 as hereinafter described, in order to optionally contain the flexible shaft 9 in a disinfectant solution or in a dry state inside the container 12, as desired. A ring support 25 encircles the wall 14 of the container 12 and in a preferred embodiment is characterized by an outer surface 26, an inner surface 27, a bottom surface 28 and a top surface 29. Height adjustment of the container 12 within the ring support 25 is achieved by means of oppositely-disposed thumb screws 31, each of which are provided with thumb screw threads 32 which register with threaded holes 30, extending from the outer surface 26 of the ring support 25 through the inner surface 27, to contact the wall 14 of the container 12 and secure the container 12 in a desired position with respect to the ring support 25. The thumb screws 31 are provided with flat heads 33 which are easily grasped and manipulated to either tighten or loosen the threaded ends of the thumb screws 31 against opposite areas of the wall 14.

Referring now to FIGS. 1, 3 and 4 of the drawing, each of the telescoping legs 35 are characterized by a top segment 36 and a bottom segment 37, which is fitted telescopically inside the top segment 36. An adjusting ring 38 is threadibly fitted to one end of each of the top segments 36, in order to tighten the bottom segments 37 telescopically inside the top segments 36, respectively, as illustrated in FIG. 3, and thereby adjust the height of the ring support 25 with respect to a supporting surface. The opposite end of each of the top segments 36 are each fitted with a threaded end 39, which registers with cooperating ring threads 34, extending into the ring support 25 from the bottom surface 28, in order to removably attach each of the telescoping legs 35 in spaced relationship, to the ring support 25. In a preferred embodiment of the invention, three such telescoping legs 35 are each attached in spaced relationship to the ring support 25 at a slight angle with respect to the vertical, as illustrated in FIG. 4, in order to orient the ring support 25 at a selected height above a supporting surface. In a most preferred embodiment of the invention, non-skid tips 40 are also provided on the extending ends of each of the bottom segments 37 of the telescoping legs 35, in order to prevent sliding of the endoscope container and support apparatus 1 with respect to the supporting surface.

It will be appreciated from a consideration of the drawing that the endoscope container and support apparatus of this invention provides a useful expedient for supporting the control head 3 and both containing and sterilizing the flexible shaft 9, of a flexible endoscope 2. Accordingly, a sterilizing solution such as betadine can be placed in the container 12, the stopper 17 sealed tightly against the O-ring 16 in the open end of the container 12 and the distal end 10 of the flexible shaft 9 inserted through the hollow yoke rest 20 and into the interior of the container 12. As the flexible shaft 9 is continually fed through the yoke rest 20, the distal end 10 contacts the curved bottom 13 and is caused to traverse the curved path defined by the curved bottom 13 and back upwardly in a loop, to the configuration illustrated in FIG. 1. In a most preferred embodiment of the invention the container 12 is slightly longer from the curved bottom 13 to the lip 15, than one-half the length of the flexible shaft 9. This expedient insures that the entire flexible shaft 9 will fit in a container 12 of appropriate size when shaped into a loop, as illustrated in FIG. 1. However, it will be appreciated that a flexible shaft 9 which is longer than twice the length of the container 12 will fit into the container 12 by additional manipulation of the flexible shaft 9 through the yoke rest 20 and into the container 12. Accordingly, under these circumstances, continued upward movement of the distal end 10 of the flexible shaft 9 causes the distal end 10 to contact the bottom of the stopper base 19 and to again curve downwardly toward the curved bottom 13. Further continued feeding of the flexible shaft 9 through the yoke rest 20 results in a coiling of the flexible shaft 9 near the curved bottom 13 of the container 12. Accordingly, a flexible shaft 9 of substantially any length can be completely immersed in disinfecting solution located in a container 12 of the endoscope container and support apparatus 1 and confined in a relatively small area, in order to completely and efficiently disinfect the flexible shaft 9 of the flexible endoscope 2. This looping or coiling effect of the flexible shaft 9, depending upon the relative lengths of the container 12 and the flexible shaft 9, as described above, is completed when the body 4 of the flexible endoscope 2 is positioned between and rests on the support fingers 23 of the yoke rest 20. Alternatively, the flexible shaft 9 can be inserted into a dry container 12 without using a disinfecting solution, under circumstances where the flexible endoscope 2 is to be stored and the flexible shaft 9 is not to be disinfected. Disinfecting solution can be added to the container 12 at any time, both while the container 12 is empty and after a flexible endoscope is placed in position as illustrated in FIG. 1, by either removing the stopper 17 or pouring the solution into the container 12 through the hollow yoke rest 20.

Other features of the endoscope container and support apparatus of this invention will be understood by again referring to the drawing, wherein it is apparent that the container 12 can be adjusted with respect to and within the ring support 25 by adjusting the opposing thumb screws 31. Furthermore, the height of the ring support 25 can also be adjusted with respect to a supporting surface, by adjustment of the adjusting rings 38 and each of the bottom segments 37 with respect to the top segments 36, respectively, of the telescoping legs 35. In this regard, and in a most preferred embodiment of the invention, as illustrated in FIG. 4, the telescoping legs 35 are threadibly inserted in the ring support 25 in an outwardly angular relationship, in order to position each of the non-skid tips 40 outwardly of the plane of the outer perimeter of the ring support 25, to further stabilize the endoscope container and support apparatus 1. Accordingly, in another most preferred embodiment of the invention, during construction of the ring support 25 the ring threads 34 are manufactured in angular relationship, extending into the ring support 25 from the bottom surface 28, in order to achieve this result. It will be further appreciated that the container 12 need not be cylindrical in shape, but can be provided with a cross-sectional configuration of desired shape and proportion, as desired. Furthermore, the container 12 need not be transparent, although transparency is desired, in order to facilitate viewing of the interior of the container 12 to determine at a glance whether a disinfecting solution is located therein, and if so, whether the disinfecting solution needs changing. However, in a most preferred embodiment of the invention the container 12 is cylindrical in configuration and is shaped from a clear plastic, glass or other transparent material generally in the shape of a test tube, with the open top having a circular shaped lip 15, as illustrated in FIG. 1 of the drawing. Regardless of the cross-sectional shape or material of construction of the container 12, it will be appreciated that the material must be capable of withstanding sterilizing temperatures up to 275° F., or be resistant to certain sterilizing gases known to those skilled in the art. Furthermore, the curved bottom 13 of the container 12 must be sufficiently curved to facilitate guiding the distal end 10 of the flexible shaft 9 in a curved path which allows the flexible shaft 9 to loop or to extend into one or more coils, as illustrated in FIG. 1 and as heretofore described. Accordingly, in yet another most preferred embodiment of the invention, the radius of curvature of the curved bottom 13 should be equal to one-half of the diameter of the container 12, in order to insure smooth traversal of the curved bottom 13 by the distal end 10 and the remainder of the distal portion of the flexible shaft 9.

It will be further appreciated by those skilled in the art that while the instant invention has been characterized and described as an "endoscope container and support apparatus", it can equally well be used to contain and support substantially any medical diagnostic or surgical apparatus having a control head or member and a flexible shaft or tube. For example, the apparatus of this invention can be used to contain and support other fiberoptic scopes such as flexible fiberoptic bronchoscopes and like diagnostic devices.

While the preferred embodiments of the invention have been described above, it will be recognized and understood that various modifications may be made therein and the appended claims are intended to cover all such modifications which may fall within the spirit and scope of the invention.

Having described my invention with the particularity set forth above, what is claimed is:

1. A fiberoptic scope container and support apparatus for supporting a fiberoptic scope having a control head and a flexible shaft, comprising;
    (a) a container having a rounded bottom and an open top;
    (b) closure means closing said open top and an opening in said closure means, said opening communicating with the interior of said container;
    (c) support means supporting said container; and
    (d) a hollow yoke rest extending through said opening in said closure means, one end of said yoke rest communicating with the interior of said container and a slot provided in the opposite end of said yoke rest, to receive the control head of the fiberoptic scope and wherein said container is generally tubular in configuration.

2. The fiberoptic scope container and support apparatus of claim 1 wherein said container is substantially transparent.

3. The fiberoptic scope container and support apparatus of claim 1 wherein said closure means is a stopper and further comprising an O-ring positioned between said stopper and said top of said container.

4. The fiberoptic scope container and support apparatus of claim 1 wherein:
   (a) said container is substantially transparent; and
   (b) said closure means is a stopper and further comprising an O-ring positioned between said stopper and said top of said container.

5. The fiberoptic scope container and support apparatus of claim 1 wherein said support means further comprises a ring encircling said container and at least three legs extending downwardly from said ring in spaced relationship for supporting said ring.

6. The fiberoptic scope container and support apparatus of claim 1 wherein:
   (a) said container is substantially transparent and is generally tubular in configuration; and
   (b) said support means further comprises a ring encircling said container and at least three legs extending downwardly from said ring in spaced relationship for supporting said ring.

7. The fiberoptic scope container and support apparatus of claim 6 wherein said closure means is a stopper and further comprising an O-ring positioned between said stopper and said top of said container.

8. The fiberoptic scope container and support apparatus of claim 7 wherein said legs are each telescopically adjustable.

9. The fiberoptic scope container and support apparatus of claim 8 further comprising at least one retainer means carried by said ring and engaging said container for retaining said container in a selected position inside said ring.

10. An endoscope container and support apparatus for supporting a fiberoptic scope having a control head and a flexible shaft extending from the control head, comprising;
    (a) a container having a rounded bottom and an open top;
    (b) closure means inserted in said top of said container;
    (c) hollow fiberoptic scope support means extending through said closure means and having one end projecting above said closure means and the opposite end communicating with the interior of said container;
    (d) a ring encircling said container and at least three legs threadibly carried by said ring in spaced relationship, said legs extending downwardly from said ring for supporting said ring, whereby the flexible shaft is inserted through said fiberoptic scope support means and oriented in said container and the control head is supported by said one end of said fiberoptic scope support means.

11. The endoscope container apparatus of claim 10 further comprising a pair of retainer means threadibly carried by said ring in oppositely-disposed relationship and engaging said container for adjustably retaining said container inside said ring.

12. An endoscope container and support apparatus for supporting an endoscope having a control head and a flexible shaft extending from the control head, comprising:
    (a) a generally cylindrically-shaped, substantially transparent container having a rounded bottom and an open top;
    (b) a stopper closing said open top;
    (c) a hollow yoke rest extending through said stopper, one end of said yoke rest communicating with the interior of said container and the opposite end of said yoke rest projecting above said stopper, and a saddle-shaped slot provided in said opposite end to receive the control head of the endoscope when the flexible shaft is projected through the yoke rest and is inserted in the interior of said container; and
    (d) a ring encircling said container; retaining means carried by said ring and engaging said container for slidably adjusting said container with respect to said ring; and at least three legs extending in spaced, angular relationship from said ring for supporting said ring and said container.

13. The endoscope container apparatus of claim 12 wherein said legs are each further characterized by a top segment, a bottom segment inserted in said top segment in telescoping relationship and an adjusting ring threadibly associated with said top segment, whereby said bottom segment of each of said legs is telescopically adjustable within said top leg for adjusting the height of said ring.

14. The endoscope container apparatus of claim 13 wherein said retaining means is a pair of thumbscrews threadibly carried by said ring in oppositely-disposed relationship.

* * * * *